United States Patent
Paolizzi

[19]

[11] Patent Number: 5,476,504
[45] Date of Patent: Dec. 19, 1995

[54] MUSCLE ELECTROSTIMULATION DEVICE FOR PASSIVE GYMNASTICS, IN PARTICULAR FOR FACIAL COSMETICS

[75] Inventor: Marco Paolizzi, Rimini, Italy

[73] Assignee: Vupiesse Italia S.A.S. Di Valentini e Paolizzi E C., Rimini, Italy

[21] Appl. No.: 169,507

[22] Filed: Dec. 17, 1993

[51] Int. Cl.$^6$ ............................................. A61N 1/18
[52] U.S. Cl. ................................................ 607/150; 601/21
[58] Field of Search ................ 128/639; 607/144, 607/145, 148, 149, 150, 151, 153, 48; 601/15, 17, 129, 154, 122, 20, 19, 21, 94, 98, 101, 102, 103, 105, 110, 113, 154, 159; 604/26

[56] References Cited

U.S. PATENT DOCUMENTS

| | | | |
|---|---|---|---|
| 870,927 | 11/1907 | Boyd | 607/150 |
| 4,033,356 | 7/1977 | Hara | 607/150 |
| 4,062,364 | 12/1977 | Masaki | 607/153 |
| 4,326,508 | 4/1982 | Stauffer | 601/129 |
| 4,811,726 | 3/1989 | Goncalves et al. | 601/154 |
| 4,858,600 | 8/1989 | Gross et al. | 601/131 |
| 5,090,402 | 2/1992 | Bazin et al. | 601/17 |
| 5,105,802 | 4/1992 | Pokorny | 601/154 |
| 5,131,384 | 7/1992 | Obagi | 601/154 |
| 5,159,922 | 11/1992 | Mabuchi et al. | 601/110 |

FOREIGN PATENT DOCUMENTS 917207  5/1991  Germany ..................... 607/146

*Primary Examiner*—Lee S. Cohen
*Assistant Examiner*—Brian M. Green
*Attorney, Agent, or Firm*—Dvorak and Traub

[57] ABSTRACT

The invention has particular application in the field of passive gymnastics, especially that of facial cosmetics, and comprises a case equipped with a workhead provided with electrodes and a handgrip arranged at an angle to each other. The electrodes (5) are positioned on the workhead (3) in such a way as to be arranged along a line (9) forming an acute angle α with a centre-line (10) of the said handgrip (4).

12 Claims, 2 Drawing Sheets

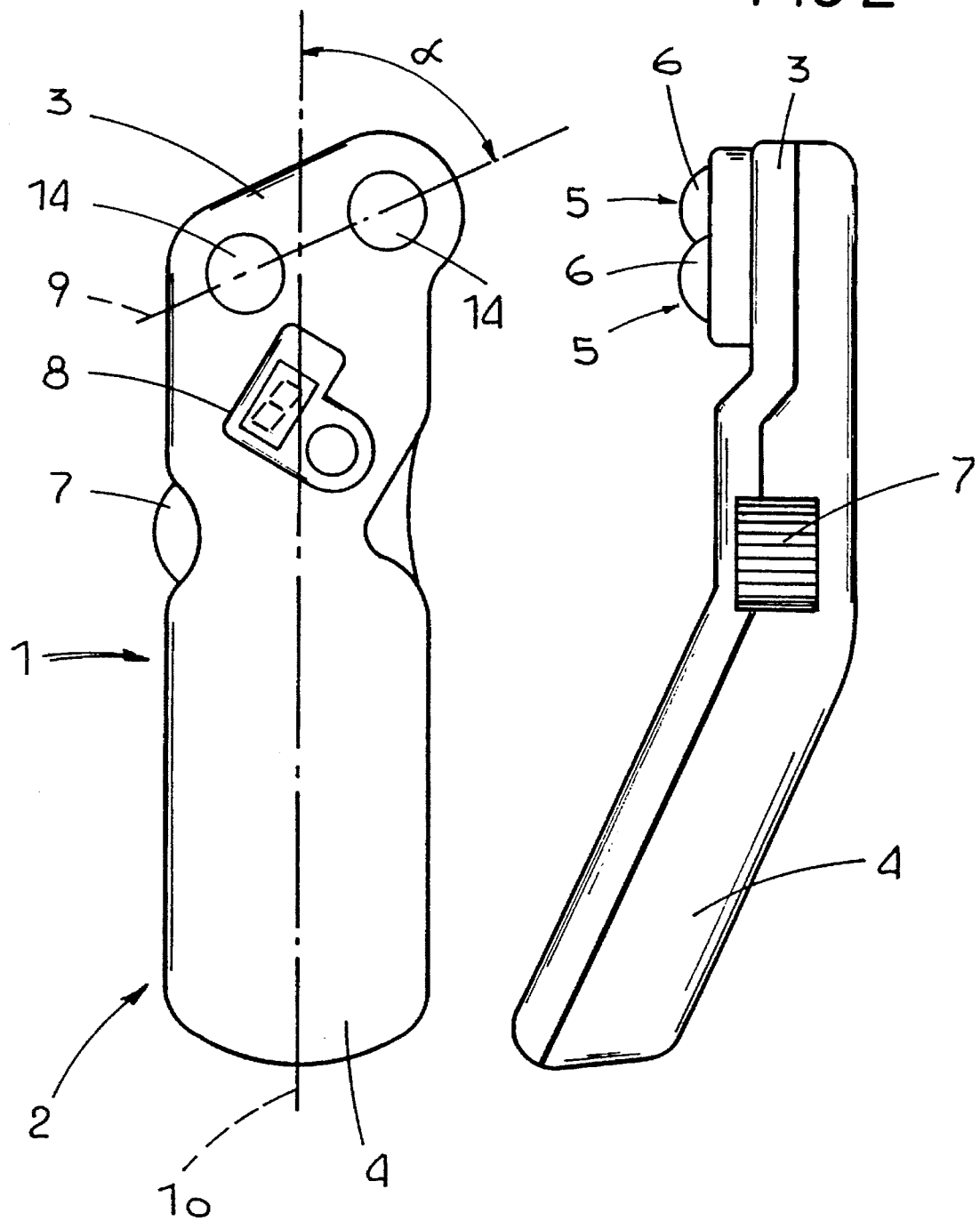

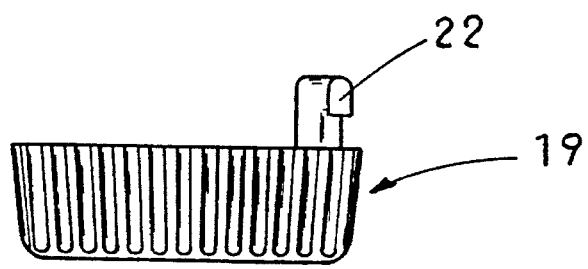
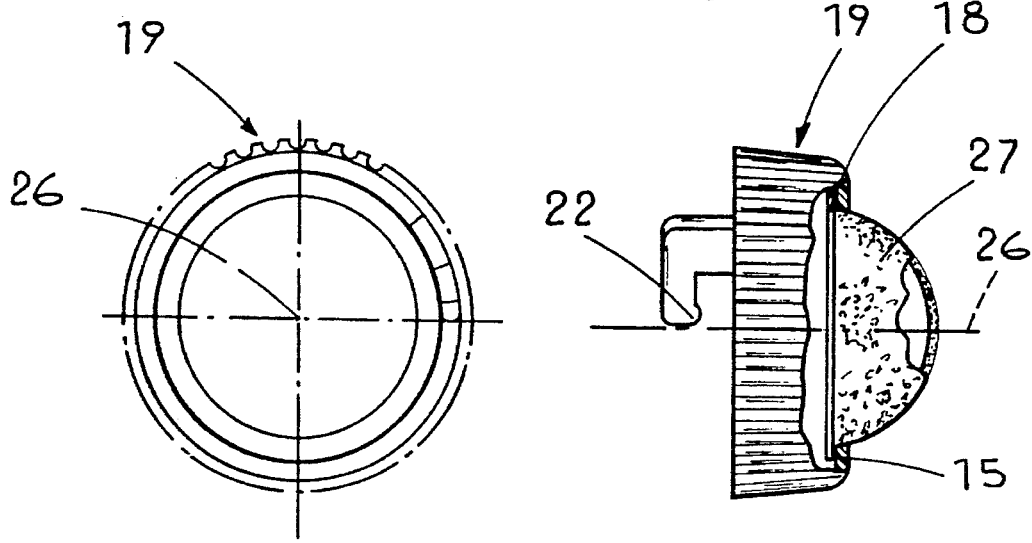
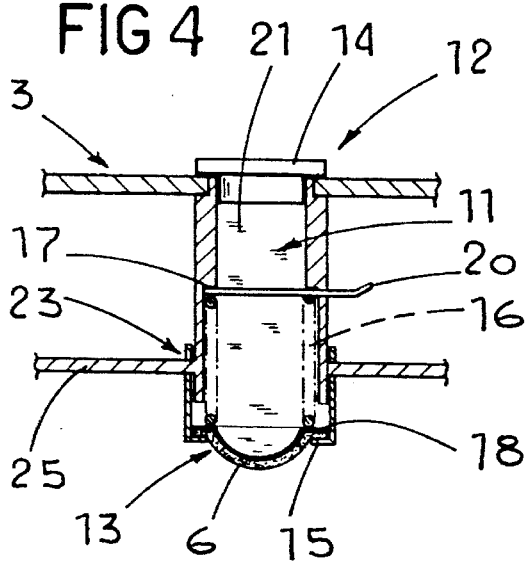
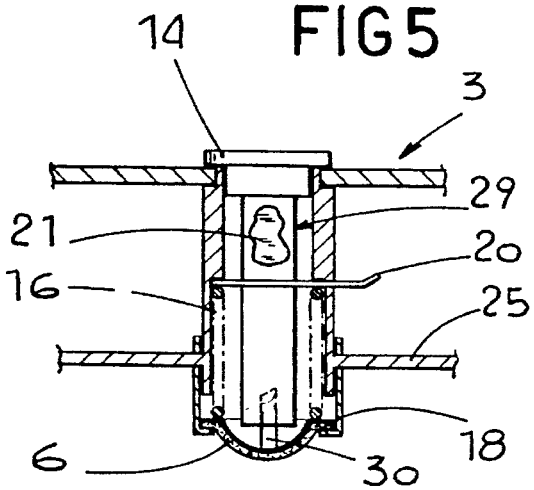

MUSCLE ELECTROSTIMULATION DEVICE FOR PASSIVE GYMNASTICS, IN PARTICULAR FOR FACIAL COSMETICS

BACKGROUND OF THE INVENTION

The invention relates to a muscle electrostimulation device for passive gymnastics, in particular for facial cosmetics, comprising a case equipped with a workhead equipped with electrodes and a handgrip which are reciprocally arranged at an angle.

In the field of facial cosmetics several devices are known which electrically stimulate the muscle bundles of the face, which devices, using a pair of electrodes placed in contact with the skin and connected to a microcurrent generator, appropriately pulsed and thus innocuous, determine an involuntary rhythmic contraction of the facial muscles (passive gymnastics) which is aimed at offering the user a recuperation of facial muscle tone and an aid to moderating facial aging lines. In prior art devices, the electrodes, which have a metallic conducting surface, are located on the work head and project from the device case. Furthermore, they conduct the electric current through the body of the user by means of the interposition of a conducting gel which is spread on the user's skin before the electrostimulator is applied.

The electrodes are reciprocally aligned, transversally to a plane passing through the symmetry axis of the case handgrip, forming a right angle with respect to the said plane.

The fundamental drawback of the prior art electrostimulation devices lies in the fact that, due to the arrangement of the electrodes on the head, during use the stimulation of the facial muscles is of scarse efficiency.

Indeed, since the handgrip of the device is angled with respect to the head, in order to provide an ergonomic grip during use of the device, because of the above-mentioned orthogonal situation, the result is that the electrodes become arranged, during use, in a position which is substantially horizontal to the face, and thus is arranged not entirely correspondingly with the substantially vertical development of the facial muscles.

A further drawback of the prior art electrostimulator devices lies in the fact that, in order to function, they require the use of conducting gel which is unpleasant on the skin for most users, with the removal operation also being distasteful.

The aim of the present invention, as it is characterised in the claims that follow, is thus that of obviating the above-mentioned drawbacks.

SUMMARY OF THE INVENTION

The invention solves the problem of providing a muscle electrostimulation device for passive gymnastics, in particular for facial cosmetics, comprising a support case for a workhead equipped with a handgrip which is angled with respect to the head itself and having electrodes on the said head which are aligned in such a way as to form an acute angle with respect to the halfway point plane of the handgrip determining, correspondingly, a substantially vertical location of the electrodes during the use of the device.

The head of the device and the electrodes are further conformed in such a way that the said electrodes self-serve of a conducting liquid contained in corresponding cavities made in the head itself.

The fundamental advantage of the invention consists essentially in the fact that the special arrangement of the electrodes permits a more efficient and rational stimulation of the face muscles.

A second advantage consists in the fact of not requiring the use of a conducting gel, but simply using a liquid which, apart from not being distasteful for the user and not fouling the constituent parts of the device, can be dosed strictly according to the specific needs of the user.

BRIEF DESCRIPTION OF THE DRAWINGS

Further characteristics and advantages of the present invention will better emerge from the detailed description that follows, of an embodiment of the invention, herein illustrated purely in the form of a non-limiting example in the accompanying figures, in which:

FIG. 1 shows the invention according to a frontal view of the whole;

FIG. 2 shows the invention according to a lateral view of the whole;

FIG. 3 shows a constituent particular of the invention shown respectively according to a plan view, a perspective view and a lateral view;

FIG. 4 shows an electrode of the invention represented in full view but transversally sectioned;

FIG. 5 shows a further embodiment of the electrode of FIG. 4, shown in a transversally-sectioned view of the whole.

DESCRIPTION OF THE PREFERRED EMBODIMENTS

With reference to the figures, FIG. 1 shows a device 1 for muscular electrostimulation for passive gymnastics, in particular for facial cosmetics, comprising a case 2, preferably of plastic material, equipped with a workhead 3 and a handgrip 4 reciprocally angled one to the other.

The said angle (FIG. 2) has the aim of enabling the workhead 3 to be located correctly with respect to the skin during use, allowing the handgrip 4 to be griped comfortably at the same time.

The workhead 3 supports a pair of electrodes 5 which project from the case 2 and are equipped with metallic conducting surfaces 6, which surfaces are cupola-shaped and electrically connected to a conventional microcurrent pulse generator, not shown in the figures, contained internally to the case 2 and activatable by means of an appropriate on-off and treatment time-selection button 7, the time value being visualised by a display or visualiser 8 situated on the case 2 of the device 1.

The electrodes 5 are located on the workhead 3 in such a way as to be arranged along a line 9 forming an acute angle (α) of about 65.5 degrees with a centre-line plane 10 of the handgrip 4 (FIG. 1).

The said value of angle α permits, when gripping the handgrip 4, a substantially vertical arrangement of the electrodes, corresponding to the development of the facial muscles.

With reference to FIG. 4, it can be seen that the workhead 3 is crossed by tubular chambers 11 for containing a conducting liquid 21.

The said chambers 11 are closed at their opposite ends 12, 13, on one side by a moveable cap 14 for the reintegration of the liquid, and on the other side by the said conducting surface 6 of the electrodes 5. The said conducting surface 6 is interpositioned between an annular collar or projection 15 of a ring-nut 19, frontally meeting a peripheral edge 18 of the conducting surface 6, and a spring 16 associated to a channel 17 of the tubular chamber 11.

The conducting surface 6 is elastically pressed against the projection 15 of the ring-nut 19, realising thus a watertight seal of the chambers 11 between the projection 15 and the peripheral edge 18 of the conducting surface 6 itself when the device 1 is in the rest condition; but instead determining the exit of the conducting liquid 21 from the chambers 11 when the device 1 is pressed against the skin of the user.

A conductor 20 of electricity, preferably having a circular crown shape, arranged crossing the chambers 11, between the channel 17 and the spring 16, allows the electrical current to reach the conducting liquid 21 which ensures the conduction of the electrical current up to the conducting surface 6 of the electrodes 5. Naturally the device 1 functions correctly in the absence of the conducting liquid 21, since, in such a case, the conduction of the electrical current is effected through the spring 16, interpositioned between the conducting surface 6 and the conductor 20 itself. With reference to FIG. 3 it can be observed that the ring-nut 19 is movable with respect to the workhead 3 so as to permit of easy cleaning and maintenance of the electrodes 5. For this purpose the ring-nut 19 is equipped with a shaped appendage 21, arranged projectingly, equipped with a transversal prong 22 which can be inserted into a correspondingly shaped channel 23, cut on a wall 25 of the workhead 3 so as to be stably but movably fixed there after the rotation of the said ring-nut 19 about its own symmetry axis.

FIG. 3 also shows that the conducting surface 6 of the electrodes 5 is preferably covered with a layer 27 of spongy material which is humidified by the conducting liquid 21 and keeps the conducting surface 6 continually dampened during the use of the device 1.

The invention as it is conceived herein is susceptible to numerous modifications and variations, all falling within the field of the inventive idea. Further, all the details can be substituted by technically equivalent ones.

For example, the liquid 21 can be constituted by water; however it is understood that this conducting liquid 21 could advantageously be constituted by a cosmetic product packed and contained in cartridges 29 of the type with breakable membrane opening.

The said cartridges 29 could be inserted, as shown in FIG. 5, internally to the chambers 11 in which case the conducting surface 6 of the electrodes 5 could be made in such a way as to envisage a pointed appendage 30 turned internally to the chambers 11 so as to determine the breaking of the membrane 29 when the said membrane is pressed posteriorly by means of the cap 14 against the conducting surface itself.

What is claimed is:

1. A muscle electrostimulation device for passive gymnastics for facial cosmetics, comprising:

a case with a workhead and a hand grip;

at least two tubular chambers, each chamber disposed in the workhead and closed at a first end by a removable cap; a liquid disposed in each tubular chamber; a ring nut with an annular collar disposed on a second end of each tubular chamber;

an electrode corresponding to each tubular chamber, each electrode having a metallic conducting surface and a peripheral edge, a portion of the electrode disposed between the second end of the corresponding tubular chamber and the annular collar of the corresponding ring-nut; and a spring disposed in each tubular chamber biasing the peripheral edge of the corresponding electrode against the annular collar of the corresponding ring-nut, wherein the peripheral edge of each electrode may be separated from the annular collar of the ring-nut to release liquid from the corresponding tubular chamber by applying pressure to the conducting surface of the electrode.

2. A device, as in claim 1, wherein the workhead and the handgrip form an angle that is approximately 65.5 degrees.

3. A device as in claim 1, wherein each electrode exhibits a cupola-shaped conducting surface.

4. A device as in claim 1, wherein the conducting surface of each electrode is coated with a layer of spongy material which spongy material is kept constantly humidified by the liquid.

5. A device as in claim 4, wherein the liquid is water.

6. A device as in claim 4, wherein the liquid is a liquid for cosmetic use.

7. A device as in claim 1, comprising internally to each tubular chamber, a cartridge which contains a cosmetic product, the cosmetic product is the liquid wherein the metallic conducting surface includes a pointed appendage projecting into the tubular chamber for piercing the cartridge when the cartridge is disposed in the tubular chamber and pressed against the pointed appendage.

8. A device as in claim 1, wherein a corresponding electrical conductor contacts each spring to conduct electricity to the electrode through the spring.

9. A device as in claim 8, wherein each electrical conductor is interpositioned between a channel and the spring.

10. A device as in claim 1, wherein the ring-nut is equipped with a projecting appendage having a transversal prong engagable with a complementarily-shaped channel disposed in a wall of the workhead, wherein the ring-nut is removably engagable with the workhead upon rotation of the ring-nut.

11. A device as in claim 1 wherein each corresponding electrical conductor positioned to contact the liquid to conduct electricity to each electrode through the liquid.

12. A device as in claim 1 wherein the case includes a display means for visualizing a time value.

\* \* \* \* \*

UNITED STATES PATENT AND TRADEMARK OFFICE
CERTIFICATE OF CORRECTION

PATENT NO. : 5,476,504
DATED : December 19, 1995
INVENTOR(S) : Marco PAOLIZZI

It is certified that error appears in the above-indentified patent and that said Letters Patent is hereby corrected as shown below:

Insert item [30] to read:

Priority is claimed based on EPO Application No. 92830682.8, filed December 23, 1992.

Signed and Sealed this

Tenth Day of June, 1997

BRUCE LEHMAN

*Attest:*

*Attesting Officer*    *Commissioner of Patents and Trademarks*